United States Patent [19]
Kim et al.

[11] Patent Number: 5,770,675
[45] Date of Patent: Jun. 23, 1998

[54] CYCLIC OLIGOMERS COMPRISING M-PHENYLENE ISOPHTHALAMIDE AND POLYMERS THEREOF

[75] Inventors: Young Hwan Kim, Hockessin; Wesley Memeger, Jr., Wilmington, both of Del.

[73] Assignee: E. I. du Pont de Nemours and Company, Wilmington, Del.

[21] Appl. No.: 664,898

[22] Filed: Jun. 18, 1996

Related U.S. Application Data

[60] Provisional application No. 60/000,402, Jun. 21, 1995.

[51] Int. Cl.$^6$ .................................................. C08G 73/00
[52] U.S. Cl. ..................... 528/170; 528/323; 528/367; 528/371; 540/460; 564/315; 564/426; 564/428
[58] Field of Search ............................. 540/460; 564/315, 564/426, 428; 528/371, 323, 367, 170

[56] References Cited

U.S. PATENT DOCUMENTS

| | | | |
|---|---|---|---|
| 5,189,160 | 2/1993 | Memeger et al. ..................... | 540/460 |
| 5,276,131 | 1/1994 | Akkapeddi et al. .................... | 528/367 |
| 5,332,800 | 7/1994 | Arduengo, III et al. ................ | 528/367 |

OTHER PUBLICATIONS

W. Memeger Jr., et al., *Macromolecules*, 26, 3476–3484, Feb. 1993.
W. Memeger, Jr., *Polym. Prepr.*, 34, 71–72, 1993.
F. E. Elhadi et al., *Tetrahedron Lett.*, 21, 4215–4218, 1980.
T. L. Guggenheim et al., *Polymer Prepr.*, 30, 138–139, Sep., 1989.
Y. H. Kim et al., *Abstracts of the 35th IUPAC Inter. Symposium on Macromolecules, University of Akron*, Jul. 11–15, 1994.

*Primary Examiner*—P. Hampton-Hightower

[57] ABSTRACT

Disclosed herein are cyclic oligomers comprising substituted or unsubstituted m-phenylene isophthalamide, complexes of these oligomers with selected metal salts, novel methods for their preparation, and polymerization of the cyclic oligomers to linear aramids. The aramids are useful, for example, as fibers for fire resistant clothing. Aminofinctional cyclic oligomers may be reacted with polyfunctional acyl halides to produce polyamides.

22 Claims, 1 Drawing Sheet

CYCLIC OLIGOMERS COMPRISING M-PHENYLENE ISOPHTHALAMIDE AND POLYMERS THEREOF

This application claims the priority benefit of U.S. Provisional Application 60/000,402 filed Jun. 21, 1995.

FIELD OF THE INVENTION

Described herein are cyclic oligomers comprising substituted or unsubstituted m-phenylene isophthalamides, their preparation, their complexes with certain metals salts, and their polymerization to corresponding linear polyamides.

TECHNICAL BACKGROUND

Cyclic oligomers with repeat units corresponding to condensation polymers such as polyesters and polycarbonates are known. These cyclic oligomers can often be converted to their corresponding linear polymers by ring-opening polymerization. Cyclic oligomers of some aromatic amides have been made.

Cyclic oligomers of (substituted) p-phenylene terephthalamide have been prepared. See, for example, W. Memeger Jr., et al., *Macromolecules*, vol. 26, p. 3476–3484 (1993) and *Polym. Prepr.*, vol. 34, p. 71–72 (1993). No cyclic meta-substituted aromatic amides are disclosed in this paper.

F. E. Elhadi, et al., *Tetrahedron Lett.*, vol. 21, p. 4215–4218 (1980) reports the synthesis of N-substituted cyclic trimers of m-aminobenzoic acid. Cyclic oligomers of diamines and dicarboxylic acids are not mentioned.

T. L. Guggenheim, et al., *Polyner Prepr.*, vol. 30, p. 138–139 (1989) report the attempted synthesis of the cyclic oligomer of m-phenylene isophthalamide by a high dilution reaction procedure, but they report no "appreciable amount of cyclic formation".

Y. H. Kim, et al., Abstracts of the 35th IUPAC International Symposium on Macromolecules, University of Akron, Jul. 11–15, 1994, report the synthesis of a nitro-substituted cyclic oligomer of m-phenylene isophthalamide. Also reported is a metal salt complex of this cyclic oligomer.

SUMMARY OF THE INVENTION

This invention concerns a cyclic oligomer of the formula

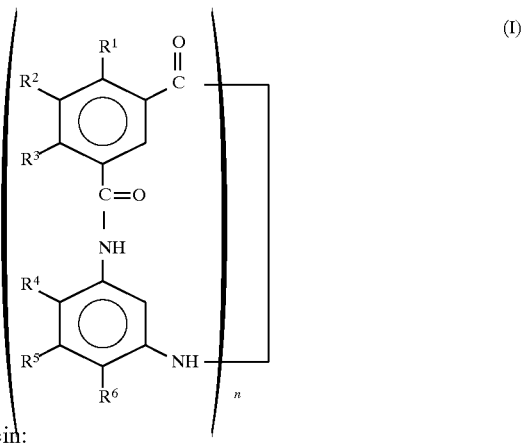

wherein:
n is an integer ranging from 3 to 12;
each of $R^1$, $R^2$, and $R^3$ is independently hydrogen, halogen, hydrocarbyl containing 1 to 6 carbon atoms, or nitro; and
each of $R^4$, $R^5$, and $R^6$ is independently hydrogen, halogne, or hydrocarbyl containing 1 to 6 carbon atoms.

This invention also concerns a complex between a cyclic oligomer of the formula

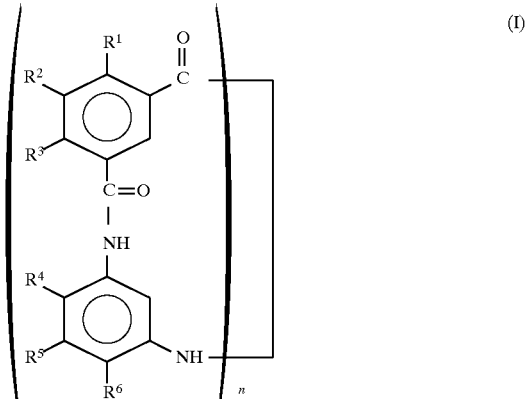

and a metal chloride, wherein said metal is selected from the group consisting of calcium, barium, strontium and the transition metals, wherein:
n is an integer ranging from 3 to 12;
each of $R^1$, $R^2$, and $R^3$ is independently hydrogen, halogen, hydrocarbyl containing 1 to 6 carbon atoms, or nitro; and
each of $R^4$, $R^5$, and $R^6$ is indendently hydrogen, halogen, or hydrocarbyl containing 1 to 6 carbon atoms.

Also described herein is a process for the preparation of a cyclic oligomer, comprising contacting a first solution of a compound of the formula

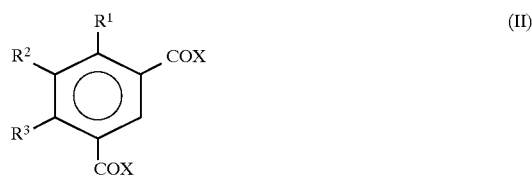

with a second solution of a compound of the formula

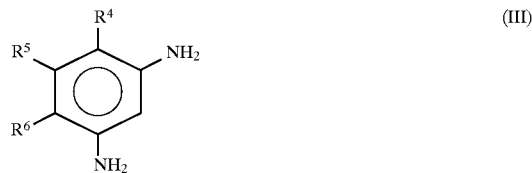

wherein
X is halogen;
each of $R^1$, $R^2$, and $R^3$ is independently hydrogen, halogen, hydrocarbyl containing 1 to 6 carbon atoms, or nitro; and
each of $R^4$, $R^5$, and $R^6$ is hydrogen, halogen, or hydrocarbyl containing 1 to 6 carbon atoms;
wherein said contacting is done with agitation or mixing; the concentration of (II) in said first solution is about 0.1 molar or less; and
the concentration of (III) in said second solution is about 0.1 molar or less.

This invention also includes a process for the polymerization of a cyclic oligomer with a base which is capable of removing an amido hydrogen atom from said cyclic oligomer. Suitably, the polymerization is carried out at a temperature of about 150° C. to about 380° C. in an inert liquid medium.

Also disclosed herein is a polymer, which is a reaction product of a compound of the formula

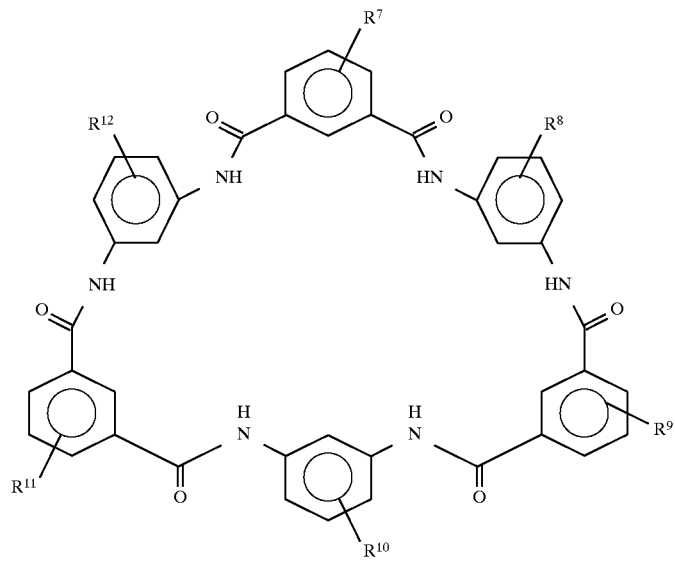

with a compound of the formula (V)

$R^{13}(COX)_2$ 

wherein each $R^7$, $R^8$, $R^9$, $R^{10}$, $R^{11}$, and $R^{12}$ is independently amino or hydrogen;

$R^{13}$ is hydrocarbylene, X is halogen, provided that:
a total of at least two of $R^7$, $R^8$, $R^9$, $R^{10}$, $R^{11}$, and $R^{12}$ are amino;
the molar ratio of (V):(IV) is at least about 1: 1; and
the molar ratio of (V):(IV) is such that number of equivalents of COX groups in the reaction does not substantially exceed the number of amino groups.

DETAILS OF THE INVENTION

Figure 1:
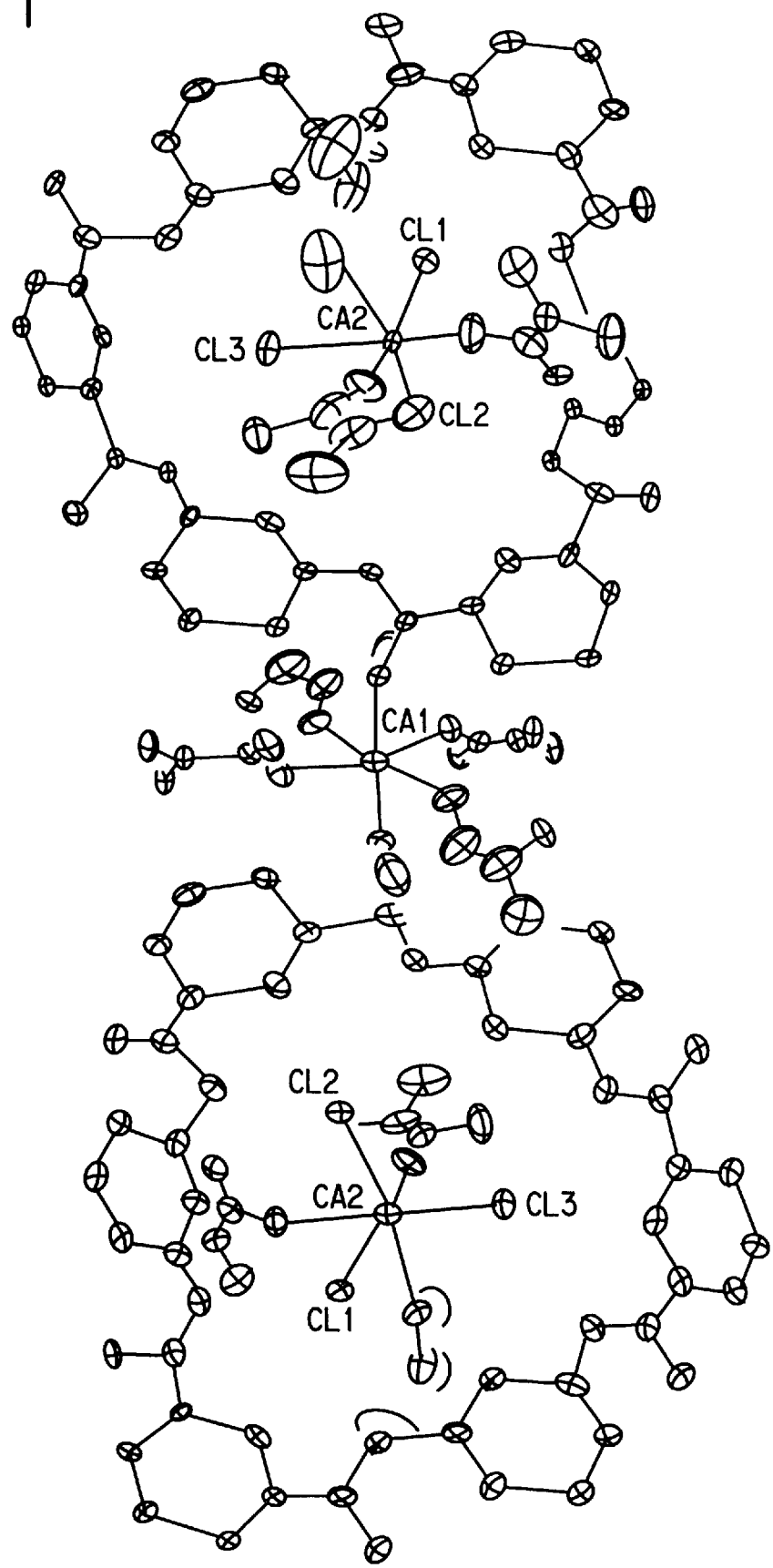
FIG. 1 is the structure of the CaCl$_2$ complex of compound (I) above, wherein n=3 and $R^1$, $R^2$, $R^3$, $R^4$, $R^5$ and $R^6$ are all hydrogen, based on X-ray crystallography (see Example 13 below).

Disclosed herein are cyclic oligomers of the formula (I) above, which are cyclic oligomers, analogous to a polyamide, comprising substituted or unsubstituted m-phenylene isophthalamide. In compounds of formula (I), it is preferred that $R^1$, $R^2$, $R^3$, $R^4$, $R^5$, and $R^6$ are all hydrogen. In another preferred embodiment of formula (I), the groups $R^1$, $R^3$, $R^4$, $R^5$, and $R^6$ are all hydrogen, and $R^2$ is nitro. It is also preferred that n is 3 (cyclic trimer). By hydrocarbyl herein is meant a univalent radical containing only carbon and hydrogen, preferably containing 1 to 6 carbon atoms, more preferably 1 to 4.

These cyclic oligomers form complexes with certain metal salts. Such a complex may be formed by mixing a cyclic oligomer with a solution of the metal salt in a solvent or, alternatively, by forming the cyclic oligomer in the presence of the metal salt. The complex may be converted back to the (simple) cyclic oligomer and free metal salt by washing the complex with a solvent for the salt such as water. Mixtures of solvents may also be used, and mixtures of the above mentioned and similar solvents with water are preferred. The preferred complexes have the same formula for the cyclic oligomer as in the preferred cyclic oligomers by themselves (described above). Preferred metal salts are calcium chloride and ferric chloride.

FIG. 1 shows the structure of a complex wherein n is 3, $R^1$, $R^2$, $R^3$, $R^4$, $R^5$, and $R^6$ are all hydrogen, and the metal salt is calcium chloride.

The cyclic oligomers described herein may be made by high dilution reaction techniques known in the art as being particularly useful for producing cyclic compounds. See, for instance, L. F. Feiser, et al., Organic Chemistry, 3rd Ed., Reinhold Publishing Corp. New York, 1956, p. 318–320, which is hereby incorporated by reference. Dilute solutions of the two reactants (II) and (III) are mixed with good agitation, preferably at rates such that, at any given time, the concentration of (II) and (III) are each relatively low and the molar amounts of (II) and (III) in the solution are approximately equal. This will usually mean that the molar rate of addition of (II) and (III) to the process will be approximately equal. Solutions of (II) and (III) may be simultaneously added to a portion of the solvent with agitation, as illustratd by Examples 1–8 below. In another method, dilute solutions of (II) and (III) are directly mixed together with good agitation in an impinging flow mixing tee.

Preferred solvents for the synthesis of the cyclic oligomers are those normally used for the synthesis of aramids, such as N,N-dimethylformamide, N,N-dimethylacetamide, N-methylpyrrolidone, and hexamethylphosphoramide. Especially preferred are N-methylpyrrolidone and N,N-dimethylacetamide. The concentration of (II) and (III) in the first and second solutions respectively are each about 0.1 molar or less, preferably each about 0.01 molar or less. The temperature at which the process is carried out is not critical, a range of −5° C. to about +50° C. being convenient, preferably about −5° C. to about +5° C.

According to the present process, it is preferred that $R^1$, $R^2$, $R^3$, $R^4$, $R^5$, and $R^6$ are all hydrogen, or that $R^1$, $R^3$, $R^4$, $R^5$, and $R^6$ are all hydrogen and $R^2$ is nitro.

In the process for forming the cyclic oligomers comprising m-phenylene isophthalamide, it has been found helpful to include in the solution in which the cyclic oligomer is forming a metal salt, as defined above. It is believed that the metal salt acts something like a "template" to increase the yield of cyclic oligomer. The salts which are used and preferred above for the metal salt complex of the cyclic oligomers are also useful and preferred in the process for the synthesis of the cyclic oligomers. The initial products, when these salts are present, are the salt complexes of the cyclic oligomers. As described above, they are readily converted to the cyclic oligomers themselves.

The cyclic oligomers may be converted to the corresponding linear polymers by contacting the cyclic oligomers with a base capable of removing an amido hydrogen atom from the cyclic oligomer (the "first polymerization"). By this is meant that the base is basic enough to remove the hydrogen atom from the group —CO—NH— which is present in the cyclic oligomer. Suitable bases include, for example, those having a hydride anion, as in sodium hydride, an amide anion, as in potassium or sodium amide, or an alkoxide, as in sodium methoxide. Alkali metal hydride and alkoxides are preferred bases. Only a catalytic amount of base need be used, about 15 molar percent or less based on the amount of cyclic oligomer present. During polymerization, it is preferred that $R^1$, $R^2$, $R^3$, $R^4$, $R^5$, and $R^6$ are all hydrogen. In other words, the cyclic oligomer of m-phenylene isophthalamide is polymerized to form poly(m-phenylene isophthalamide).

The first polymerization is carried out at a temperature of about 150° to about 380° C., preferably about 150° to about 300° C. It is suitably carried out in an inert liquid medium, which may or may not dissolve the cyclic oligomer and/or basic catalyst. Suitable inert liquid media include N,N-dimethylformamide, N,N-dimethylacetamide, N-methylpyrrolidone, diphenyl sulfone, tetramethylenesulfone, and the like, wherein N-methylpyrrolidone and diphenyl sulfone are preferred. In order to avoid undesired side reactions, particularly of the base present, it is preferred that the process be carried out under an inert gas such as nitrogen or argon, and that the starting materials be reasonably dry.

The product of the first polymerization, poly(m-phenylene isophthalamide), and its substituted analogs, are aramids which are useful for making fire resistant garments, particularly of use to firefighters. The cyclic oligomer may also be used to sequester certain metal salts or to remove them from waste streams. The cyclic oligomers are also useful as a high temperature additive for polymers. The metal salt complexes may be used as source of the metal salts, as when used for melting ice.

In a second polymerization, an amino functional cyclic amide (IV), as defined above, is reacted with a difunctional acyl halide (V), as also defined above. When only two of $R^7$, $R^8$, $R^9$, $R^{10}$, R 1, and $R^{12}$ are amino, a linear polyamide is produced wherein the cyclic amide moieties derived from (IV) alternates with the moieties derived from (V). When more than two of $R^7$, $R^8$, $R^9$, $R^{10}$, $R^{11}$, and $R^{12}$ are amino, a crosslinked thermoset polymer will be produced if most of the amino groups are reacted with acyl halide groups. In the second polymerization, it is preferred that $R^7$, $R^9$, and $R^{11}$, the substitutents on the ring derived from the diacid, are amino, and/or all of $R^8$, $R^{10}$, and $R^{12}$, the substituents on the ring derived from the diamine, are all hydrogen. It is also prefered that X is chlorine and that a sufficient amount of (V) is added so that at least 75 mole percent of the amino groups present are reacted. If a thermoplastic, the polymer may be used as a molding resin. If it is not thermoplastic and/or crosslinked, it may be used as a thermoset resin. In both cases, parts for electrical equipment, especially useful at high temperature, may be made.

In the Examples, the following abbreviations are used:
DMAc-N,N-dimethylacetamide
DMF-N,N-dimethylfornamide
I-isophthalic
ICI-isophthaloyl chloride
MPD-m-phenylenediamine
NMP-N-methylpyrrolidone
NMR-nuclear magnetic resonance spectroscopy

EXAMPLE 1

Preparation of a Cyclic Trimer Complex

Isophthaloyl chloride (10.2 g) and 5.4 g of m-phenylenediamine were dissolved in 50 mL each of toluene and DMAc, respectively. These solution were slowly added with agitation to 200 mL of DMAc containing 5.55 g of $CaCl_2$ in a 500 mL three neck round bottom flask which is cooled by a ice bath. Total addition took 60 min. The solution was stirred for two more hours, then poured to a mixture of 200 mL of methanol and 100 mL water. The precipitate was washed and dried at 100°C. under vacuum to give 11.25 g of crude product. This solid was recrystallized from 50 mL DMAc containing 5.5 g of $CaCl_2$ and 2 mL water, to give 2.31 g of product, which is found to be a pure complex of cyclic trimer and $CaCl_2$.

In a separate experiment, the reaction mixture was neutralized with $Ca(OH)_2$ with similar results.

EXAMPLES 2–3

Preparation of Cyclic Trimer and Complex

Examples 2–4 were run in a similar way to Example 1. Results are in the Table below.

| Example | Salt | Salt weight (g) | [salt] [Amide] | DMAc Solvent (ml) | Weight of Complexed Crystal |
|---|---|---|---|---|---|
| 2 | No salt | NA | NA | 300 | 0.57 |
| 3 | $CaCl_2$ | 5.55 | 1.0 | 300 | 0.27 |

* All experiments were conducted with 10.15 g of ICI in 70 mL toluene and 5.40 g of MPD in 70 mL DMAc solvent, otherwise as the procedure described in Example 1.

EXAMPLES 4–8

Preparaton of Cyclic Trimer and Complex

The procedure described in Example 1 was repeated, except NMP was used as the solvent. Results are shown in the Table below.

| Example | Salt | Salt weight (g) | [salt] [Amide] | NMP Solvent (ml) | Weight of Complexed Crystal |
|---|---|---|---|---|---|
| 4 | No salt | NA | NA | 300 | 1.395 |
| 5 | $CaCl_2$ | 2.78 | 0.5 | 300 | 1.354 |
| 6 | $CaCl_2$ | 8.32 | 1.5 | 300 | 1.922 |
| 7 | $CaCl_2$ | 5.55 | 1.0 | 100 | 0.584 |
| 8 | $FeCl_3$ | 8.11 | 1.0 | 300 | 5.305 |

* All experiments were conducted with 10.15 g of ICI in 50 mL toluene and 5.40 g of MPD in 50 mL NMP solvent, otherwise as the procedure described in Example 1.

EXAMPLE 9

Ring Opening Polymerization of MPD-I Cyclic Trimer

To 4.6 mL of NMP containing 0.002 g of sodium hydride (0.083 mmol) was added the cyclic trimer (0.450 g, 0.63 mmol), which caused evolution of gas, then heated to 100°C. The mixture was opaque with a slight yellow color. After 30 min, 0.0097 g of N-acetyl-epsilon-caprolactam (0.063 mmol) in 0.5 mL of NMP was added, and then the temperature was set for 210° C. After about 2 hours, a small layer of translucent liquid was observed above an opaque off-white mixture below which exhibited a slight increased viscosity. After 4 hours, when the reaction mixture consisted of a well dispersed white solid in the solvent, it was allowed to cool to RT (room temperature) and filtered, then washed with water and finally dried in a vacuum oven at 100° C. Total 0.42 g of polymer with 0.104 dL/g inherent viscosity (0.5 wt % at 30° C. in 98.5% $H_2SO_4$) was obtained.

EXAMPLE 10

Ring Opening Polymerization of MPD-I Cyclic Trimer

To 4.1 g of phenylsulfone containing 0.002 g of sodium hydride (0.083 mmol) was added the cyclic trimer (0.448 g, 0.63 mmol), then heated to 150° C., where the solvent melted and gas was evolved. The mixture turned opaque within 1 hour. The vessel was cooled to room temperature, and 0.0097 g of N-acetyl-epsilon-caprolactam (0.063 mmol) in 0.5 mL of phenyl sulfone was added. Then the mixtureit was slowly heated to 265° C. for one hour. The solid was transferred to an Erlenmeyer flask after cooling, and washed with hot MeOH to remove the phenyl sulfone then with hot water. The polymer was obtained by filtration, followed by vacuum drying at 100°C. in a vacuum oven. Total 0.42 g of polymer with 0.17 dL/g inherent viscosity (0.5 wt % at 30° C. in 98.5% $H_2SO_4$) was obtained.

EXAMPLE 11

Dissolution of $CaCl_2$ from the Cyclic Complex

A $CaCl_2$ complex (100 mg) of a cyclic $CaCl_2$ complex obtained by the procedure described in Examples 1–8 was treated with copious amount of deionized water overnight to give 51 mg of light tan colored material. A NMR analysis indicated that the it has lost about 50% of complexed $CaCl_2$.

EXAMPLE 12

Dissolution of $CaCl_2$ from the Cyclic Complex $CaCl_2$ can be completely washed out from the complex prepared by the procedure described in Examples 1–8. The $CaCl_2$ complex of a cyclic product was first treated with DMF, then washed with 3N HCl for 10–15 minutes three times, followed by three times washing a mixture of DMF and water. An elemental analysis detected no chlorine.

EXAMPLE 13

Recrystallization of $R^2=NO_2$ Cyclic $CaCl_2$ Complex

A crude cyclization product of $R^2=NO_2$, which was obtained by a method similar to that described in Example 1, was repeatedly precipitated into water from a DMAc solution. This product (44 mg) was dissolved in 4.0 g of DMF containing 27 mg of $CaCl_2$, and then the flask was placed in a closed chamber containing THF at the bottom. Single crystals suitable for X-ray were formed in 3–4 days. The x-ray structure showed that two cyclic trimers are stacked each other with respect to each other 60° out of plane, and a $CaCl_6^{-4}$ ion is complexed inside of the pocket of the cyclic compounds through hydrogen bonding between chloride and amide hydrogen.

A cyclic compound with $R^2=H$, as obtained from Example 3, was also crystallized similarly for x-ray crystallography. The crystal is a triclinic, belongs to P-1 space group with cell parameters of a=12.498, =22.729, c=12.342Å, α=99.457,β= 105.796γ=75.345°. Its structure is shown in FIG. 1. In this case the complex is formed between $CaCl_3$ and the cyclic compound. Two cyclic compounds are linked each other through a $Ca(DMF)_6^{2+}$ ion.

EXAMPLE 14

Mass Spectroscopic Analysis of Crude Cyclization Product

The crude reaction products prepared by methods similar to those of Examples 1 and 2 were compared using laser description ionization/time of flight (IDL-TOF) mass spectroscopy, by dissolving the mixture in the dimethylsufoxide and 2-(4-hydroxyphenolazo)-benzoic acid (HABA) matrix. It showed that the relative concentration of cyclic trimer gets higher when $CaCl_2$ was present in the reaction media.

EXAMPLE 15

Preparation of Nitro-Substituted Cyclic Oligomer

To a 2-L 3-necked round bottom Morton type flask equipped with a mechanically driven stirrer, $N_2$ line, and two 2500 mL dropping funnels with side return loops was added 700 mL DMAc (dried over molecular sieves). Meta-phenylene diamine (MPD) (10.81 g) in 100 mL DMAc and 5-nitroisophthaloyl chloride (24.80 g) in toluene (100 mL) were placed in the separate dropping funnels and added to the cold (ice bath) reaction flask over a period of about 4.5 hours. During the addition, the reaction mixture remained clear. The mixture was then allowed to stand for 2 days, then poured into 750 mL MeOH and 250 mL $H_2O$ contained in an Erlenmeyer flask. The fine pale yellow ppt. which separated was stirred for 2 hours, then filtered by suction through a fine fritted disc Buchner funnel. Filtration required overnight, leaving a gelatinous solvent-laden filter cake. This was washed further by slurrying with MeOH, filtered, then dried overnight in 95 vacuum oven. Upon removal from oven, it was noticed that some soft viscous material was present in the solids. The material was subsequently washed further with MeOH in a blender and filtered by suction and dried at 95° C./vac. oven. The yield was 14.1 g.

To 50.5 mL DMAc in 250 mL 3-necked round bottom flask with condenser drying tube and $N_2$ line was added 5.3 g dry $CaCl_2$. Upon heating to 150° C. in an oil bath, the $CaCl_2$ did not completely dissolve. The above product (13.6 g) was added and after heating for 2 days at 160° C., a slightly viscous slurry was obtained. DMAc (50 mL) was added and after about 1 hour a clear solution was obtained. About 30 mL of the DMAc was removed and the solution began to cloud. The mixture was allowed to cool and stand overnight at RT whereupon 1.5 cc water was added which appeared to precipitate additional solid. The solid was filtered on a fine fritted disk Buckner funnel, washed with cold DMAc, and sucked dry under $N_2$ overnight. The white powder (3.7 g) was transferred to a bottle and dried at 100° C. in a vacuum oven. The yield was 3.6 g. Another 0.4 g of product crystallized from the filtrate. The combined material (3.96 g) was boiled in 40 mL water for 2.5 hours, then filtered by suction, and then washed free of chloride with boiling water. The off-white solid was dried overnight in a 100° C. vacuum oven. The yield was 2.67 g, and 0.20 g of product was recrystallized from 15 mL DMAc. This was done by dissolving in DMAc and seeding with the crude product, followed by cooling in dry ice/acetone until the DMAc began to freeze. After standing at RT for 5 days, the crystals were collected by suction filtrate, then dried at 110° C. under vaccuum in an oven. The yield was 0.11 g. The remainder of the product was recrystallized in a similar fashion. The FAB MS of the product exhibited a peak at M+H=849.67 corresponding to the cyclic trimer.

EXAMPLE 16

Preparation of Amine-Substituted Cyclic Oligomer

To 150 mL of DMAc was added 0.1 g of 5% Pd on charcoal and to this mixture was added 2.0 g of the nitro-substituted cyclic oligomer (see above for preparation). The mixture was treated with $H_2$ at 100° C. under 130 psi for 4 hours. The catalyst and charcoal were removed by filtration and the product recovered as a solid by rotary evaporation of the DMAc. The FAB MS of the product exhibited a peak at M+H=759.94 corresponding to the amine substituted cyclic trimer.

EXAMPLE 17

Preparation of Polyamide-Containing Cyclic Oligomers of m-Phenyleneisophthalamide To 0.55 g of $CaCl_2$ in 200 mL cylindrical round bottom flask with $N_2$ line and 316-stainless steel basket stirrer was added 24.3 g of NMP and after stirring for 5 minutes, 1.25 g of the above crude amine substituted cyclic trimer was added. About 2.5 mL of NMP was used as a wash to remove the cyclic trimer from the sides of the flask but was not completely effective. A spatula was then used to scrape the material from the walls. The system was then heated to 70° C. whereupon a clear brown solution was obtained. The mixture was cooled in an ice bath for 20 minutes, and then 0.60 g terephthaloyl chloride was added all at once. The mixture gave a clear yellow gel within a few seconds, which, after a short time (minutes), fractured fairly easily. After 45 minutes, 0.092 g of $CaCl_2$ was added and stirring continued for 20 minutes more. No significant change occurred in consistency of the gel. Examination under crossed optical polarizers revealed only minor birefringence. Upon shearing, the degree of birefringence increased. NMP (5 mL) was added, stirring was continued for 5 minutes, and then another 3 mL NMP was added. The gel softened over the next 20 minutes whereupon 0.24 g $CaCl_2$ was added. After another hour, the gel exhibited appreciable flow (gel flowed away from the wall when the stirrer was stopped). More NMP (3 mL) was added and stirring continued (elapsed time 3.5 hours). After another hour, the moderately viscous mixture containing undissolved gel particle was heated to 50° C. and held overnight. After standing for several days, an aliquot (21 mL) of the mixture was centrifuged using a heated (50° C.) centrifuge. The nearly clear greenish upper layer was removed with a syringe and transferred to a glass plate, covering an area of about 4 in.×3 in. After drying overnight in a 60° C. vacuum oven and then standing under $N_2$ in an oven for 3 days, the film was surprisingly coherent and released easily when a razor blade was inserted between the film and glass. Several small strips were removed and soaked in distilled water for several hours. Pieces of the coherent films were dried between paper towels and on glassine paper, respectively, in a 90° C. vacuum oven. The uncentrifuged remainder of the mixture was precipitated by addition of water filtered by suction, and then washed twice with hot water by magnetically stirring on a hot plate. The solid was finally washed with hot 2B alcohol and dried in a 90° C. vac. oven. The product exhibited an $\eta_{inh}$ of 0.47 (conc. of 0.50 w/v % in conc. $H_2SO_4$ at 30° C.). Further, the polymer exhibited outstanding thermal stability with a TGA decomposition temperature of 400° C. in N2 (heating rate- 20° C./min.), but with 95% weight retention at 500° C.

What is claimed is:

1. A cyclic oligomer of the formula

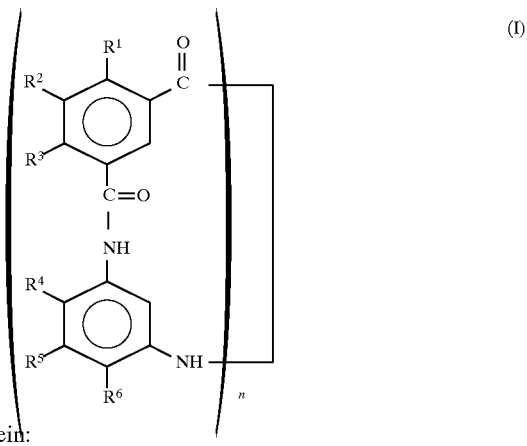

wherein:

n is an integer ranging from 3 to 12;

each of $R^1$, $R^2$, and $R^3$ is independently hydrogen, halogen, hydrocarbyl containing 1 to 6 carbon atoms, or nitro; and each of $R^4$, $R^5$, and $R^6$ is independently hydrogen, halogen, or hydrocarbyl containing 1 to 6 carbon atoms.

2. The cyclic oligomer as recited in claim 1 wherein $R^1$, $R^2$, $R^3$, $R^4$, $R^5$, and $R^6$ are all hydrogen.

3. The cyclic oligomer as recited in claim 1 wherein $R^1$, $R^3$, $R^4$, $R^5$, and $R^6$ are all hydrogen, and $R^2$ is nitro.

4. The cyclic oligomer as recited in claim 1 wherein n is 3.

5. The cyclic oligomer as recited in claim 2 wherein n is 3.

6. A complex between a cyclic oligomer of the formula

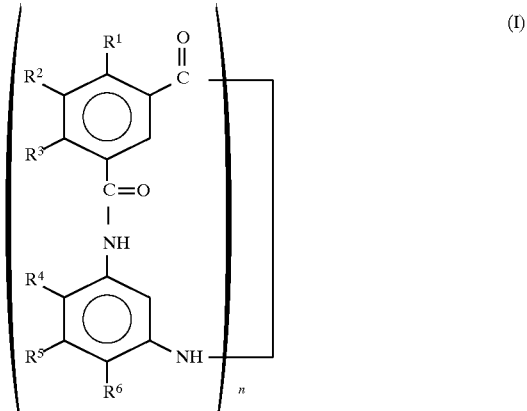

and a metal chloride, wherein said metal is selected from the group consisting of calcium, barium, strontium and the transition metals, and wherein:

n is an integer ranging from 3 to 12;

each of $R^1$, $R^2$, and $R^3$ is independently hydrogen, halogen, hydrocarbyl containing 1 to 6 carbon atoms, or nitro; and each of $R^4$, $R^5$, and $R^6$ is hydrogen, halogen, or hydrocarbyl containing 1 to 6 carbon atoms.

7. The complex as recited in claim 6 wherein $R^1$, $R^2$, $R^3$, $R^4$, $R^5$, and $R^6$ are all hydrogen.

8. The complex as recited in claim 6 wherein $R^1$, $R^3$, $R^4$, $R^5$, and $R^6$ are all hydrogen, and $R^2$ is nitro.

9. The complex as recited in claim 6 wherein said metal salt is calcium chloride or ferric chloride.

10. The complex as recited in claim 6 wherein said metal salt is calcium chloride.

11. The complex as recited in claim 7 wherein said metal salt is calcium chloride.

12. A process for the preparation of a cyclic oligomer, comprising, contacting a first solution of a compound of the formula

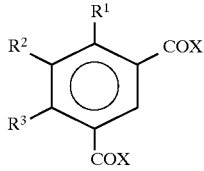

(II)

with a second solution of a compound of the formula

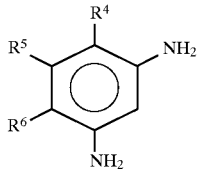

(III)

wherein:
X is halogen;
each of $R^1$, $R^2$, and $R^3$ is independently hydrogen, halogen, hydrocarbyl containing 1 to 6 carbon atoms, or nitro; and
each of $R^4$, $R^5$, and $R^6$ is independently hydrogen, halogen, or hydrocarbyl containing 1 to 6 carbon atoms;

wherein said contacting is done with agitation or mixing;
the concentration of (II) in said first solution is about 0.1 molar or less;
the concentration of (III) in said second solution is about 0.1 molar or less;
and whereby a cyclic oligomer is formed.

13. The process as recited in claim 12 wherein $R^1$, $R^2$, $R^3$, $R^4$, $R^5$, and $R^6$ are all hydrogen.

14. The cyclic oligomer as recited in claim 12 wherein a cyclic trimer is produced.

15. The process as recited in claim 12 wherein a metal chloride is present, wherein said metal is selected from the group consisting of calcium, barium, strontium and the transition metals.

16. The process as recited in claim 15 wherein said metal chloride is calcium chloride or ferric chloride.

17. The process as recited in claim 15 wherein said metal chloride is calcium chloride, and $R^1$, $R^2$, $R^3$, $R^4$, $R^5$, and $R^6$ are all hydrogen.

18. A process for the polymerization of a cyclic oligomer of m-phenylene isophthalamide, comprising contacting, in an inert liquid medium, said cyclic oligomer with a base which removes an amido hydrogen atom from said cyclic oligomer.

19. The process as recited in claim 18 wherein said base is an alkali metal hydride.

20. The process as recited in claim 18 carried out at about 150° C. to about 380° C., and wherein said inert liquid medium is diphenyl sulfone.

21. The complex as recited in claim 6 wherein n=3.

22. The complex as recited in claim 7 wherein n=3.

* * * * *